(12) United States Patent
Hui et al.

(10) Patent No.: US 11,344,503 B2
(45) Date of Patent: May 31, 2022

(54) CARIPRAZINE RELEASE FORMULATIONS

(71) Applicant: HALO SCIENCE LLC, Morganville, NJ (US)

(72) Inventors: Yu Hui, Winston Salem, NC (US); Kevin Yuan, Morganville, NJ (US); Tian Zhang, Richmond (CA)

(73) Assignee: HALO SCIENCE LLC, Morganville, NJ (US)

( * ) Notice: Subject to any disclaimer, the term of this patent is extended or adjusted under 35 U.S.C. 154(b) by 103 days.

(21) Appl. No.: 16/714,539

(22) Filed: Dec. 13, 2019

(65) Prior Publication Data

US 2021/0177768 A1 Jun. 17, 2021

(51) Int. Cl.
| | |
|---|---|
| *A61K 9/50* | (2006.01) |
| *A61K 47/34* | (2017.01) |
| *A61K 9/19* | (2006.01) |
| *A61K 31/495* | (2006.01) |
| *A61K 9/51* | (2006.01) |

(52) U.S. Cl.
CPC .............. *A61K 9/5089* (2013.01); *A61K 9/19* (2013.01); *A61K 9/5084* (2013.01); *A61K 9/5153* (2013.01); *A61K 9/5192* (2013.01); *A61K 31/495* (2013.01); *A61K 47/34* (2013.01)

(58) Field of Classification Search
CPC ...... A61K 9/5089; A61K 9/5084; A61K 9/19; A61K 9/5153; A61K 9/5192; A61K 9/0019; A61K 9/1647; A61K 47/34; A61K 31/495
See application file for complete search history.

(56) References Cited

U.S. PATENT DOCUMENTS

2016/0257661 A1 9/2016 Taddei et al.

FOREIGN PATENT DOCUMENTS

| EP | 3231418 A1 | 10/2017 |
|---|---|---|
| WO | 2014083522 A1 | 6/2014 |
| WO | 2017034991 A1 * | 3/2017 |
| WO | 2018229641 A1 | 12/2018 |
| WO | 2019106490 A1 | 6/2019 |

* cited by examiner

*Primary Examiner* — Carlos A Azpuru
(74) *Attorney, Agent, or Firm* — Rimon P.C.

(57) ABSTRACT

The patent discloses long-term injectable formulations and delivery systems of cariprazine and related salts and derivatives in the prevention and treatment of various psychotic diseases, such as schizophrenia, mania, and bipolar disorder. The dosage forms are either microsphere, microparticle, nanoparticle drug delivery systems in a pharmaceutically acceptable carrier, or devices that contain long-term injectable formulation of such cariprazine and related salts and derivatives.

10 Claims, 3 Drawing Sheets

CARIPRAZINE RELEASE FORMULATIONS

BACKGROUND

Cariprazine is dopamine D2 and D3 receptor partial agonist which is used as an antipsychotic drug for schizophrenia, mania, and bipolar disorder. However, the current drug delivery method has only immediate release oral dosage forms, which is not convenient to these types of patients. Currently, there is no long-term formulation of cariprazine microsphere, or nanoparticle formulation or delivery system available to provide extended drug release, dosing convenience and high patient compliance. Therefore, there is a great need to develop a long acting formulation or extended-release drug delivery system to provide convenience and compliance.

It is well accepted that zero-order release of active ingredients from a formulation produces a steady and predictable pharmacokinetic profile. For extended drug delivery system, zero-order release makes a drug concentration falling within a therapeutic window for longer period of time. This is especially beneficial for psychiatric patients because reduced frequency of pharmaceutical administration mitigates patient noncompliance and a defined pharmacokinetic profile lowers the risks of adverse reactions and improves the clinical responses, where negative and positive symptoms of psychosis need to be treated concurrently with a delicate balance.

However, there are very few examples of formulations that possess characteristics of zero-order release. For the most microsphere or microparticle or nanoparticle formulations, the drug release profile will be more than likely a burst release and a first-order drug release because the outer shell of the particle has larger surface area and matrix disintegration is faster in the beginning and early phase of drug release. Furthermore, the molecules of active ingredient are typically smaller than the matrix component, the diffusion of smaller molecules across the eroded matrix in contact with dissolution media expedites the drug release in the beginning of dissolution. These two drug release mechanisms in polymer matrix account for the "burst release" of active ingredient and increased release in the early phase of drug release profile or first-order release, therefore result in undesirable spike and erratic drug concentrations during treatment.

BRIEF SUMMARY

Current available cariprazine is formulated in conventional solid dosage form, such as capsules, that discharges cariprazine into digestive tracts directly when mixed with gastric or intestine fluid. It requires patients to swallow the capsules or tablets every day during the treatment period, which pose a challenge to this special population of patients. In addition, it also has some side effects such as abdominal pain, vomiting, diarrhea, nausea, constipation, and etc. No one has reported an extended microsphere or nanoparticle formulation or long acting drug delivery system of cariprazine, which can be given to patients intramuscularly (I.M.) and provide long duration of pharmacological effect, convenience, and high patient compliance. Accordingly, it is a primary object of the invention to address the above-mentioned need in the art by providing microparticle or nanoparticle formulation or drug delivery system of cariprazine and related salts and other derivatives compounds.

It is another object of the invention to provide microparticle or nanoparticle formulation comprising cariprazine and related salts and other derivatives compounds with zero-order release profiles because zero-order release offers much more therapeutic benefits than the first-order release and other release types as stated above.

It is another object of the invention to avoid the initial burst release and spikes of drug release in the early stage.

It is another object of the invention to provide a dosage form for the administration of cariprazine and related salts and other derivatives compounds in microparticle and nanoparticle formulations to potentially avoid GI and other side effects.

It is another object of the invention to provide such a dosage form comprised of nanoparticle dosage forms with the drug.

It is another object of the invention to provide such microspheres or microparticles, nanoparticles suspending in a liquid or semi-solid carrier.

Additional objects, advantages and novel features of the invention will be set forth in part in the description which follows, and in part will become apparent to those skilled in the art upon examination of the following, or may be learned by practice of the invention.

In still another aspect of the invention, a method is provided for treating a patient having a condition that is responsive to administration of an active agent selected from cariprazine and related salts and other derivatives, thereof, the method comprising intramuscularly administering to the patient, within the context of an effective dosing regimen, a pharmaceutical formulation as described above, i.e., microspheres, microparticles, and nanoparticles. The condition generally involves schizophrenia, mania, bipolar disorder, and other related disease.

In often included embodiments, a pharmaceutical composition is provided comprising a therapeutically effective amount of an active agent selected from cariprazine, a salt thereof, or a derivative thereof including a derivative salt form thereof, a biodegradable and biocompatible polymer comprising a polymeric matrix material, and a non-ionic water soluble colloid, wherein the active agent is ionically complexed with the biodegradable and biocompatible polymer and the active agent is dispersed in the matrix material, and wherein the composition is in the form of a microparticle, a microsphere, a nanoparticle, or a combination thereof. Often, the cariprazine, salt thereof, or derivative thereof including a derivative salt form thereof is present in the composition at a concentration of between about 0.1% to about 80% wt/wt. Also often, the biodegradable and biocompatible polymer is selected from the group consisting of poly(lactic) acid, poly(glycolic) acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, albumin, casein, lipids, and waxes. Frequently, the non-ionic water soluble colloid is selected from the group consisting of one or more of poly(vinyl alcohol), polysorbate, lecithin, carboxymethyl cellulose, gelatin, poly(vinyl pyrrolidone), Tween 80, Tween 20, or Span. And, often the non-ionic water soluble colloid is selected from the group consisting of one or more of poly(vinyl alcohol), polysorbate, lecithin, carboxymethyl cellulose, gelatin, poly(vinyl pyrrolidone), Tween 80, Tween 20, or Span. In frequent embodiments, the cariprazine, salt thereof, or derivative thereof including a derivative salt form thereof is present in the composition at a concentration of between about 0.1% to about 80% wt/wt; wherein the biodegradable and biocompatible polymer is selected from the group consisting of poly(lactic) acid, poly(glycolic) acid, copolymers of the foregoing, poly(aliphatic carboxylic acids), copolyoxalates, polycaprolactone, polydioxonone, poly(ortho carbonates), poly(acetals), poly (lactic acid-caprolactone), polyorthoesters, poly(glycolic acid-caprolactone), polyanhydrides, albumin, casein, lipids, and waxes; wherein the non-ionic water soluble colloid is selected from the group consisting of one or more of poly(vinyl alcohol), polysorbate, lecithin, carboxymethyl cellulose, gelatin, poly(vinyl pyrrolidone), Tween 80, Tween 20, or Span, wherein the composition comprises a collection of microparticles, microspheres, nanoparticles, or a combination thereof, and wherein the collection comprises one or more discreet populations of microparticles, microspheres, or nanoparticles, each discreet population of microparticles, microspheres, or nanoparticles defined an average diameter size that is different than another of the two or more discreet populations of microparticles, microspheres, or nanoparticles. According to frequent embodiments of the present disclosure, the microparticle, the microsphere, the nanoparticle, or the combination thereof exhibits desirable drug release profile. Often, the microparticle, the microsphere, the nanoparticle, or the combination thereof exhibits zero order release characteristics.

In frequent embodiments, the pharmaceutical composition comprises a collection of microparticles, microspheres, nanoparticles, or a combination thereof. In frequent embodiments, the collection comprises a population of microparticles, microspheres, or nanoparticles defined an average diameter size. Often, the collection comprises two or more discreet populations of microparticles, microspheres, or nanoparticles, each discreet population of microparticles, microspheres, or nanoparticles defined an average diameter size that is different than another of the two or more discreet populations of microparticles, microspheres, or nanoparticles.

Also in frequent embodiments, the biodegradable and biocompatible polymer comprises a poly (d,l lactic co-glycolic acid) and poly(d,l-lactic acid) (d,l-PLA) copolymer, a poly(d,l-lactide-co-glycolide) copolymer, a poly (lactic acid), a poly (glycolic acid), or combination thereof. Often in such embodiments, the copolymer is poly(d,l-lactide-co-glycolide) and the molar ratio of lactide to glycolide in the copolymer is between about 95:5 to about 5:95.

Also contemplated according the present disclosure are methods for producing sustained-release microparticles and nanoparticles. Such methods often including steps of: dissolving an active agent and one or more biodegradable and biocompatible polymers in a solvent that is not highly soluble in water and has a boiling point below 100° C. to form an organic phase; quenching the organic phase with a non-ionic water-soluble colloid polymer in water to form a quenched composition; homogenizing the quenched composition to form an emulsion; and removing the solvent from the emulsion to form a microparticle, microsphere or nanoparticle, wherein the active agent is selected from the group consisting of cariprazine, a salt thereof, or a derivative thereof including a derivative salt form thereof. Often according to such methods, the solvent comprises one solvent for both the biodegradable and biocompatible polymers and active ingredient, or a blend of different solvents, wherein one is a solvent for the biodegradable and biocompatible polymers, and another solvent is a solvent for the active agent. Also often, the solvent for the biodegradable and biocompatible polymers is a poorly water soluble solvent. Often, the concentration of the non-ionic water-soluble hydrophilic colloid in the process medium is between about 0.1% to about 50% by w/w.

According to certain contemplated embodiments, the solvent for the biodegradable and biocompatible polymer has a solubility for the biodegradable and biocompatible polymer of 10% to 100%.

According to further embodiments contemplated methods often further include contacting the microparticle, the microsphere or the nanoparticle with a second quenching solution. Also often, such methods also include washing the microparticle, the microsphere or the nanoparticle with a wash solution comprising a C1-C4 aliphatic alcohol. Also often, such methods also include drying the microparticle, the microsphere or the nanoparticle at a temperature of between about 10° C. to about 50° C. Also often, such methods also include freeze drying the microparticle, the microsphere or the nanoparticle in a freeze dryer or lyophilizer. Contemplated methods may include all of a sub-selection/combination of the above-noted further steps. Often according to the contemplated methods, the organic phase is combined with an aqueous phase prior to removing the solvent. Frequently, the emulsion is prepared by a homogenizer, mixer, or microfluidizer.

These and other embodiments, features, and advantages will become apparent to those skilled in the art when taken with reference to the following more detailed description of various exemplary embodiments of the present disclosure in conjunction with the accompanying drawings.

DETAILED DESCRIPTION

Figure 1:
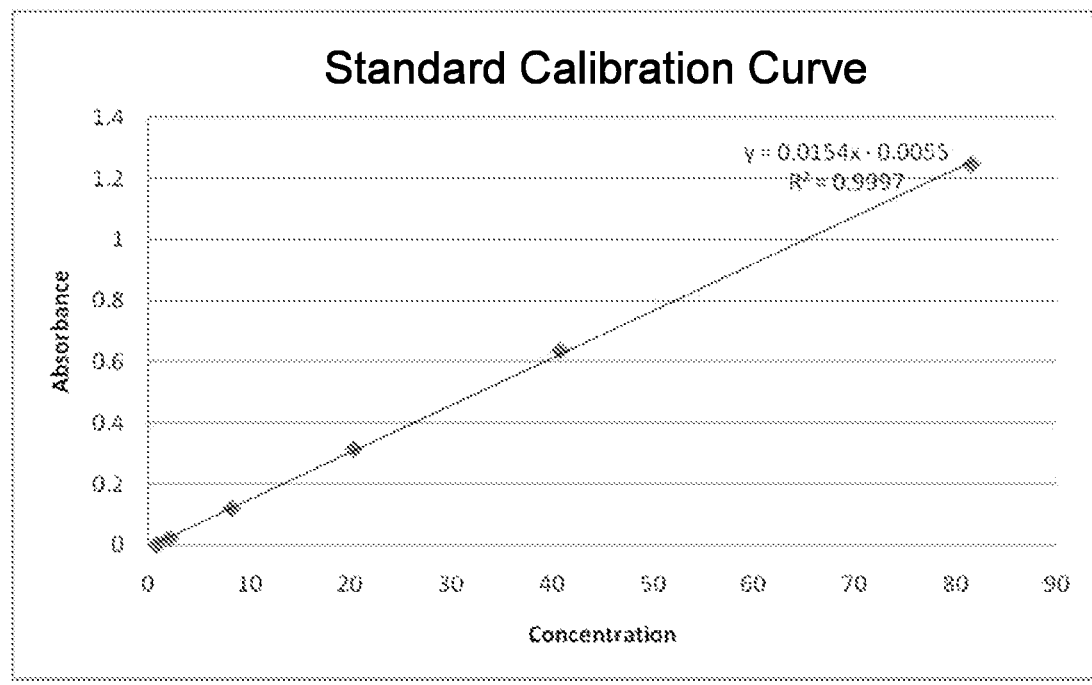
FIG. 1 depicts a graph showing the standard calibration and regression equation of cariprazine solution.

The current invention features pharmaceutical dosage forms that provide for long-acting microsphere drug delivery system or formulation of a cariprazine and related salts and other derivatives. The extended drug delivery system of cariprazine and related salts and other derivatives can be given to patients intramuscularly periodically and therefore provide long duration of pharmacological effect, convenience, and high patient compliance.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

To ensure clarity of the description that follows, the following definitions are provided. "Microparticles" or "microspheres" or "nanoparticles" mean solid particles that contain an active agent dispersed or dissolved within a biodegradable, biocompatible polymer that serves as the matrix of the particle. "Limited water solubility" means having a solubility in water in the range of from about 0.1 to about 25 wt. % at 20° C. "Halogenated hydrocarbons" mean halogenated organic solvents, i.e., C1-C4 halogenated alkanes, e.g., methylene chloride, chloroform, methyl chloride, carbon tetrachloride, ethylene dichloride, ethylene chloride, 2,2,2-trichloroethane, and the like. "Biodegradables" mean materials that should degrade by bodily processes to products readily disposable by the body and should not accumulate in the body. The products of the biodegradation should also be biocompatible with the body. "Biocompatibles" mean materials that are not toxic to the human body, is pharmaceutically acceptable, is not carcinogenic, and does not significantly induce inflammation in body tissues. "Weight %" or "% by weight" means parts of weight per total parts of weight. "Zero-order release" means the increment of drug concentration in a dissolution media over a set time interval is a constant.

In the process of the present invention, a solvent is used to produce biodegradable, biocompatible microparticles and nanoparticles comprising at least one biologically active agent. The preferred solvent system is one solvent or a blend of at least two solvents. A particularly preferred solvent is a solvent blend comprising at least two solvents. A first solvent component of the solvent blend is a poor solvent for the active agent, but is a good solvent for the biodegradable, biocompatible polymer used herein. A second solvent component of the solvent blend is a good solvent for the active agent. The active agent is dissolved or dispersed in the solvent. Polymer matrix material is added to the agent-containing medium in an amount relative to the active agent that provides a product having the desired loading of active agent. Optionally, all of the ingredients of the microparticle and nanoparticle product can be blended in the solvent blend medium together.

An ideal solvent blend for encapsulation of an active agent should have a high solubility for the polymeric encapsulating agent of generally at least about 5 weight percent and, preferably, at least about 20 weight percent at 20° C. The upper limit of solubility is not critical, but if over about 50 weight percent of the solution is encapsulating polymer, the solution may become too viscous to handle effectively and conveniently.

The solvent system, although substantially immiscible with the continuous phase process medium and any quenching liquid, which usually are water or water-based, preferably has a limited solubility therein. If the solvent system were infinitely soluble in the process medium, microparticles and nanoparticles would be unable to form during the emulsion phase; if the solubility of the solvent system in an extractive quenching medium were too low, however, large quantities of quenching medium would be needed. Generally, solvent solubilities of from about 0.1 to about 30% in the process medium and any quench medium are acceptable for use herein.

Added considerations in choosing a component of the solvent blend of the present invention include boiling point (i.e., the ease with which the solvents can be evaporated, if desired, to form finished product) and specific gravity (tendency of the discontinuous or oil phase to float during emulsifying and quenching). Finally, the solvent system should have low toxicity.

The polymer matrix material of the microparticles and nanoparticles prepared by the process of the present invention is biocompatible and biodegradable. The matrix material should be biodegradable in the sense that it should degrade by bodily processes to products readily disposable by the body and should not accumulate in the body. The products of the biodegradation should also be biocompatible with the body, as should any residual solvent that may remain in the microparticles.

Preferred examples of polymer matrix materials include poly(glycolic acid), poly(d,l-lactic acid), poly(l-lactic acid), copolymers of the foregoing, and the like. Various commercially available poly (lactide-co-glycolide) materials (PLGA) may be used in the method of the present invention. For example, poly (d,l-lactic-co-glycolic acid) is commercially available from Evonik (Birmingham, Ala.). Suitable products commercially available from Evonik or other suppliers are 50:50, 65:35 DL, 75:25 DL, 85:15 DL poly (d,l lactic co-glycolic acid) and poly(d,l-lactic acid) (d,l-PLA). These copolymers are available in a wide range of molecular weights and ratios of lactic acid to glycolic acid.

The most preferred polymer for use in the practice of this invention is the copolymer, poly(d,l-lactide-co-glycolide). It is preferred that the molar ratio of lactide to glycolide in such a copolymer be in the range of from about 85:15 to about 15:85.

The present invention is broader than the shelf-life problem caused by residual solvent, and directed to the more general solution of washing products having particular tenacious solvent residuals with a wash liquid comprising water and a water miscible solvent for the tenacious solvent(s) in the product. The washing step affects the drug release rates from the microparticles. The residual solvent in microparticles can also be removed by evaporation, filtration, and freeze drying process. In these process, the solvents preferably are volatile with low boiling point, which enables easy and full removal of the residual solvents.

The molecular weight should be high enough to permit the formation of satisfactory polymer matrix or coatings. Usually, a satisfactory molecular weight is in the range of 5,000 to 500,000 Daltons, preferably about 150,000 to 200,000 Daltons. The molecular weight of a polymer is also important from the point of view of its influence upon the biodegradation rate of the polymer. The drug can be released from the microparticles and nanoparticles by erosion and diffusion process.

The formulation prepared by the process of the present invention contains an active agent dispersed in the microparticle and nanoparticle polymeric matrix material. The amount of such agent incorporated in the microparticles and nanoparticles usually ranges from about 1 wt. % to about 90 wt. %, preferably 20 to 50 wt. %.

In carrying out the process of the present invention, the encapsulating polymer should be essentially 100% dissolved in the solvent or solvent blend at the time the solution is emulsified. The active agent can be dispersed or dissolved in the solvent or solvent blend at the time it is added to the continuous phase process medium.

To achieve zero-order release, it is preferred the active agent (i.e. cariprazine) to complex with the encapsulating polymer, during the dissolving process in a suitable solvent. For example, a free base of cariprazine or equivalent process resulting in a free base (e.g. liquid-liquid extraction) can be used in the formulation or dissolving process to enable a thorough complexing of the active agent and the encapsulating polymer. A strong interaction between the active agent and the encapsulating polymer is important to minimize the diffusion of the active agent upon matrix erosion. For example, an ionic interaction can be used to impede the diffusion by trapping the active agent, cariprazine, in the polymeric matrix and prevent the "burst release". A solvent of choice used in the dissolving/complexing process is the one that is not readily soluble in water. Complexing takes place in a hydrophobic environment to enable complete interaction of the active agent and encapsulating polymer. And the solvent should be easy to remove during the quenching or evaporation process.

The microparticles and nanoparticles can be mixed by size or by type so as to provide for the delivery of active agent to the patient in a multiphasic manner and/or in a manner that provides different active agents to the patient at different times, or a mixture of active agents at the same time. For example, secondary antibiotics, vaccines, or any desired active agent, either in microparticle or nanoparticle form or in conventional, unencapsulated form can be blended with a primary active agent and provided to the patient.

An emulsion is created by high speed homogenization, static mixing, in line homogenization, microfluidization, and sonification. Double emulsion can also be used to create microparticles and nanoparticles.

Usually, a hydrophilic colloid is added to the continuous-phase processing medium to prevent the solvent microdroplets from agglomerating and to control the size of the solvent microdroplets in the emulsion. Examples of compounds that can be used as hydrophilic colloids include, but are not limited to, poly(vinyl alcohol), polysorbate, lecithin, carboxymethyl cellulose, gelatin, poly(vinyl pyrrolidone), Tween 80, Tween 20, Span, and the like. The concentration of hydrophilic colloid in the process medium should be sufficient to stabilize the emulsion and will affect the final size of the microparticles and nanoparticles. Generally, the concentration of the hydrophilic colloid in the process medium will be from about 0.1% to about 10% by weight based on the process medium, depending upon the hydrophilic colloid, the discontinuous or oil phase solvent system, and the processing medium used. A preferred dispersing medium combination is a 0.1 to 10 wt. %, more preferably 0.5 to 2 wt. %, solution of poly(vinyl alcohol) in water.

Not every hydrophilic colloid is suitable for producing a microparticle or nanoparticle that possesses zero-order release characteristics. A non-ionic and highly water-soluble polymer is preferred. Ionic colloid normally caused the microparticles or nanoparticles to be charged, which may result in static charge of the powder product and caused difficulties in d handling and filling in vials. The charged particles are normally not favorable for injectables and sometimes result in drug burst release due to the attracted drug molecules on the particle surface. Water soluble property of hydrophilic colloid polymer gives rise to a concentration gradient across the microparticle or nanoparticle during the emulsification/hardening process because more of such polymer are embedded on the outer shell of the particle and less of such polymer can make its way to a hydrophobic core. The hydrophilic colloid gradient across the microparticle/nanoparticle is important for zero-order release, because the erosion on the outer shell of a particle happening in the beginning of dissolution results in less available hydrophilic colloid to accelerate the drug release than an evenly dispersed hydrophobic colloid encapsulated in the polymeric particle, which can give a first-order or other types of drug release. Although poly(vinyl alcohol) is a preferred example for making such zero-order release microparticles/nanoparticles, other non-ionic water soluble polymers are obvious choices to a person skilled in the art that are taught by this invention.

The emulsion can be formed by mechanical agitation of the mixed phases or by adding small drops of the discontinuous phase that contains active agent and wall forming material to the continuous phase processing medium. The temperature during the formation of the emulsion is not especially critical, but can influence the size and quality of the microparticles and nanoparticles and the solubility of the active agent in the continuous phase. The dispersion process can be conducted at any temperature that maintains stable operating conditions, preferably from about 20° C. to about 60° C., depending upon the active agent and excipient selected.

In practice, the organic phase and the aqueous phase are mixed in a static mixer or homogenizer or microfluidizer to form an emulsion. The emulsion formed comprises microparticles and nanoparticles containing active agent encapsulated in the polymeric matrix material.

The microparticles and nanoparticles are then stirred in a tank, and organic solvent is removed by evaporation at atmospheric pressure or under vacuum. The solvent evaporation process normally takes over 12 to 24 hours to remove the solvent at atmospheric pressure. The evaporation process is normally much quicker under vacuum. The caution should be taken to avoid the overflow of liquid to the tubings of vacuum.

The microparticles and nanoparticles may also be stirred in a tank containing a quench solution in order to remove most of the organic solvent from the microparticles and nanoparticles, resulting in the formation of hardened microparticles. The extraction medium removes a significant portion of the solvent from the microparticles and nanoparticles, but does not dissolve them. During the extraction, the extraction medium containing dissolved solvent can, optionally, be removed and replaced with fresh extraction medium.

After the quench step has been completed, the microparticles and nanoparticles can be isolated as stated above, and then may, if desired, be dried by exposure to air or by other conventional drying techniques, such as, vacuum drying, drying over a desiccant, or the lyophilization, or the like. This process is very efficient in encapsulating an active agent since core loadings of up to about 80 wt. %, preferably up to about 30 wt. %, can be obtained.

Both temperature and amount of solvent spike can be adjusted to contribute beneficially to the final desired product characteristics, i.e., highly porous, quick releasing microparticles and nanoparticles, or slow releasing microparticles and nanoparticles having a low porosity.

The quench liquid can be plain water, a water solution, or other suitable liquid, the volume, amount, and type of which depends on the solvents used in the emulsion phase. The quench liquid is preferably water. Depending on the solvent system, quench volume can vary from about 2 to about 20 times the saturated volume. Additionally, it is convenient to describe the quench volume requirement relative to batch size (microparticle and nanoparticle product). This ratio can vary from about 0.1 to about 10 liters of quench volume per gram of microparticles produced.

After the solvent evaporation step or quenching step, the microparticles and nanoparticles are isolated from the aqueous quench solution by any convenient means of separation—the fluid can be decanted from the microparticles or the microparticle suspension can be filtered, for example, a sieve column can be used. Various other combinations of separation techniques, such as filtration, ultrafiltration, centrifugation, ultracentrifugation, can be used, if desired. Filtration is preferred.

The filtered microparticles and nanoparticles are then subjected to the washing step of the present invention in order to reduce further the level of residual solvent(s) therein, preferably to a level in the range of from about 0.1 to about 2.0%. Sometimes, high level of residual solvent in the microparticles and nanoparticles can be sufficient to accelerate the degradation process, thereby reducing shelf-life. Degradation of the microparticles and nanoparticles can occur, for example, by undesired hydrolysis of the hydrolyzable linkages of a matrix polymer by a basic active agent. Thus, the washing step(s) of the present invention are employed to reduce the residual benzyl alcohol or other solvent content in the microparticles and nanoparticles to retard the degradation process.

As stated above, the wash solution comprises either water alone or, preferably, water and a solvent miscible therewith that is also a good solvent for the residual solvent in the microparticles. Where, as in the preferred process of the present invention, $C_1$-$C_4$ aliphatic alcohols are preferred for use in the wash solution. These alcohols are methanol, ethanol, propanol, butanol, and isomers of the foregoing. The most preferred alcohol is ethanol. The concentration of the alcohol in the wash solution can vary depending upon the circumstances.

The temperature of the wash solution is also important to the efficiency of the washing step. Generally, increasing the temperature will decrease the time needed for the wash to lower the remaining residual content to the desired level. On the other hand, too high a temperature can be detrimental in that the softening temperature of the matrix polymer of the microparticles may be approached or exceeded, thereby causing clumping or stickiness. Conversely, too low a temperature may cause the matrix material to become too hard, thereby retarding the rate at which the residuals can be extracted, whereby the process may become prohibitively expensive. Preferably, the temperature employed will bracket room temperature, i.e., from about 10° C. to about 30° C. Where water alone is used as the wash solvent, it will be employed at an elevated temperature, i.e., above room temperature, preferably in a range of from about 25° C. to about 40° C.

Normally, it will be desirable to employ more than one wash step, typically two or three. After each such step, the microparticles and nanoparticles will be separated from the wash solution by well-known separation means, e.g., filtration, decantation, centrifugation, and the like. Filtration is preferred.

After each separation step, the microparticles and nanoparticles can, if desired, be fully or partially dried employing conventional drying means at temperatures substantially similar to those of the previous wash solution. The use of dry compressed air at temperatures ranging from about 10° C. to about 30° C. has been found especially useful and convenient and is preferred. The microparticle and nanoparticle product is usually made up of particles of a spherical shape, although sometimes the microparticles may be irregularly shaped. The microparticles and nanoparticles can vary in size, ranging from submicron to millimeter diameters. Preferably, microparticles of 1-500 microns, and nanoparticles of 1-1000 nm, are prepared, whereby administration of the microparticles to a patient can be carried out with a standard gauge needle. Preferably, the drug-loaded microparticles and nanoparticles are dispensed to patients in a single administration, releasing the drug in a constant or pulsed manner into the patient and eliminating the need for repetitive injections.

The cariparazine bearing microparticles and nanoparticles are obtained and stored as a dry material. Prior to administration to a patient, the dry microparticles and nanoparticles can be suspended in an acceptable pharmaceutical liquid vehicle, such as, a 2.5 wt. % solution of carboxymethyl cellulose, whereupon the suspension is injected into the body.

The microparticles and nanoparticles can be mixed by size or by type so as to provide for the delivery of active agent to the patient in a multiphasic manner and/or in a manner that provides different active agents to the patient at different times, or a mixture of active agents at the same time. For example, secondary antibiotics, vaccines, or any desired active agent, either in microparticle and nanoparticle form or in conventional, unencapsulated form can be blended with a primary active agent and provided to the patient.

Those skilled in the art will understand that any of the numerous active agents in addition to cariprazine that can be incorporated into microparticles and nanoparticles can be prepared by the process of the present invention. For those materials that have no groups detrimental to the integrity of the matrix polymer, the additional washing step(s) of the present invention may prove beneficial in ways, such as, controlling the release characteristics of active agent in vivo or reducing an undesirable or possibly harmful solvent.

The following examples further describe the materials and methods used in carrying out the invention. The examples are not intended to limit the invention in any manner.

Example 1. Preparation of Cariprazine Microparticles by Solvent Evaporation Method 70 mg of PLGA (50:50) polymers and 30 mg of cariprazine are dissolved in 2 mL DCM. The obtained solution is added into 20 mL of 1.0% PVA solution. Three different speeds are used to homogenize the mixture to obtain an emulsion. The magnetic stirrer is used to stir the emulsion and evaporate the DCM solvent in 12 hours. The weights and homogenization speeds are shown in Table 1.

TABLE 1

Conditions for Preparation of Cariprazine Microparticles

| Sample No. | Weight of Weighing Paper (mg) | Weight of PLGA (mg) | Weight of Cariprazine (mg) | Homogenization Speed (rpm) |
| --- | --- | --- | --- | --- |
| 1 | 34.0183 | 70.8 | 33.6 | 5000-7000 |
| 2 | 32.9224 | 78.4 | 30.5 | 9000-11000 |
| 3 | 33.4265 | 73.9 | 32.7 | 18000-20000 |

Example 2. Calibration Curve of Standard Solutions

The standard cariprazine are weighed and prepared into a series of standard solution with different concentration. The solutions are measured by a UV spectrophotometer at wavelength of 254 nm. The concentration and absorbance results are shown in Table 2. The regression equation is $Y=0.0154X-0.0055$, where Y is absorbance and X is drug concentration. The standard calibration curve is shown in FIG. 1.

TABLE 2

Calibration Curve of Standard Solutions

| Concentration (µg/ml) | Absorbance |
| --- | --- |
| 81.6 | 1.2465 |
| 40.8 | 0.6366 |
| 20.4 | 0.315 |
| 8.16 | 0.1204 |
| 2.04 | 0.0221 |
| 0.816 | 0.0004 |

Example 3. Determination of Drug Loading Percentage in Cariprazine Microparticles The drug loading percentage is determined as below. For Sample 1, Absorbance is determined as 0.4080 at 254 nm. The concentration is calculated as 26.85 µg/ml by substituting the Absorbance into the regression equation: $Y=0.0154X-0.0055$. The calculated concentration is multiplied by 25 dilution factor, and multiply 19 mL to obtain 12.75 mg. The result is the un-capsulated cariprazine in the solution. The total drug amount is 33.6 mg, therefore 20.85 mg is encapsulated in PLGA polymer. The total of PLGA is 70.8 mg, therefore, the drug loading percentage in microparticles is 20.85/(20.85+70.8)=22.75%. The drug loading percentages of Samples 2 and 3 are calculated by similar calculation and shown in Table 3.

TABLE 3

Percentages of Drug Loading in Cariprazine Microparticles

| Sample | Volume of Solution (ml) | Absorbance | Concentration (µg/ml) | Percentage of Drug Loading (%) |
|---|---|---|---|---|
| 1 | 19 | 0.4080 | 26.85 | 22.75 |
| 2 | 19.5 | 0.3654 | 24.08 | 19.31 |
| 3 | 19.5 | 0.3135 | 20.71 | 23.42 |

Example 4. Drug Release from Cariprazine Microparticles 25.8 mg of microparticles from Sample 1 are added in 25 mL PBS buffer; 23.6 mg of microparticles from Sample 2 are added in 25 mL PBS buffer; 28.1 mg of microparticles from Sample 3 are added in 25 mL PBS buffer. The suspensions of microparticles are stirred in a water bath maintained at 45 degree C. for ten day. Each day, 5 mL of drug release solution is taken and filtered by a 0.45 m membrane filter. 5 mL of PBS buffer was replenished to compensate the loss of dissolution medium. Then 1 mL of solution are accurately measured and diluted to 50 mL by methanol. The absorbance is measured at 254 nm and substituted into the regression equation to calculate released drug amount. The absorbance of each sample at different time points are shown in Table 4.

TABLE 4

The Absorbance of Released Drug from Cariprazine Microparticles in 10 Days

| Sample | 1 d | 2 d | 3 d | 4 d | 5 d | 6 d | 7 d | 8 d | 9 d | 10 d |
|---|---|---|---|---|---|---|---|---|---|---|
| 1 | 0.0114 | 0.0180 | 0.0259 | 0.0338 | 0.0423 | 0.0482 | 0.0536 | 0.0562 | 0.0572 | 0.0579 |
| 2 | 0.0069 | 0.0129 | 0.0188 | 0.0220 | 0.0286 | 0.0332 | 0.0386 | 0.0402 | 0.0413 | 0.0418 |
| 3 | 0.0087 | 0.0168 | 0.0241 | 0.0328 | 0.0396 | 0.0473 | 0.0534 | 0.0592 | 0.0646 | 0.0651 |

The amount of released drug is calculated and shown in Table 5.

TABLE 5

The Amount of Released Drug (mg) from Microparticles in 10 Days

| Sample | 1 d | 2 d | 3 d | 4 d | 5 d | 6 d | 7 d | 8 d | 9 d | 10 d |
|---|---|---|---|---|---|---|---|---|---|---|
| 1 | 1.37 | 1.91 | 2.55 | 3.19 | 3.88 | 4.36 | 4.80 | 5.01 | 5.09 | 5.15 |
| 2 | 1.01 | 1.49 | 1.97 | 2.23 | 2.77 | 3.14 | 3.58 | 3.71 | 3.80 | 3.84 |
| 3 | 1.15 | 1.81 | 2.40 | 3.11 | 3.66 | 4.29 | 4.78 | 5.25 | 5.69 | 5.73 |

Figure 2:
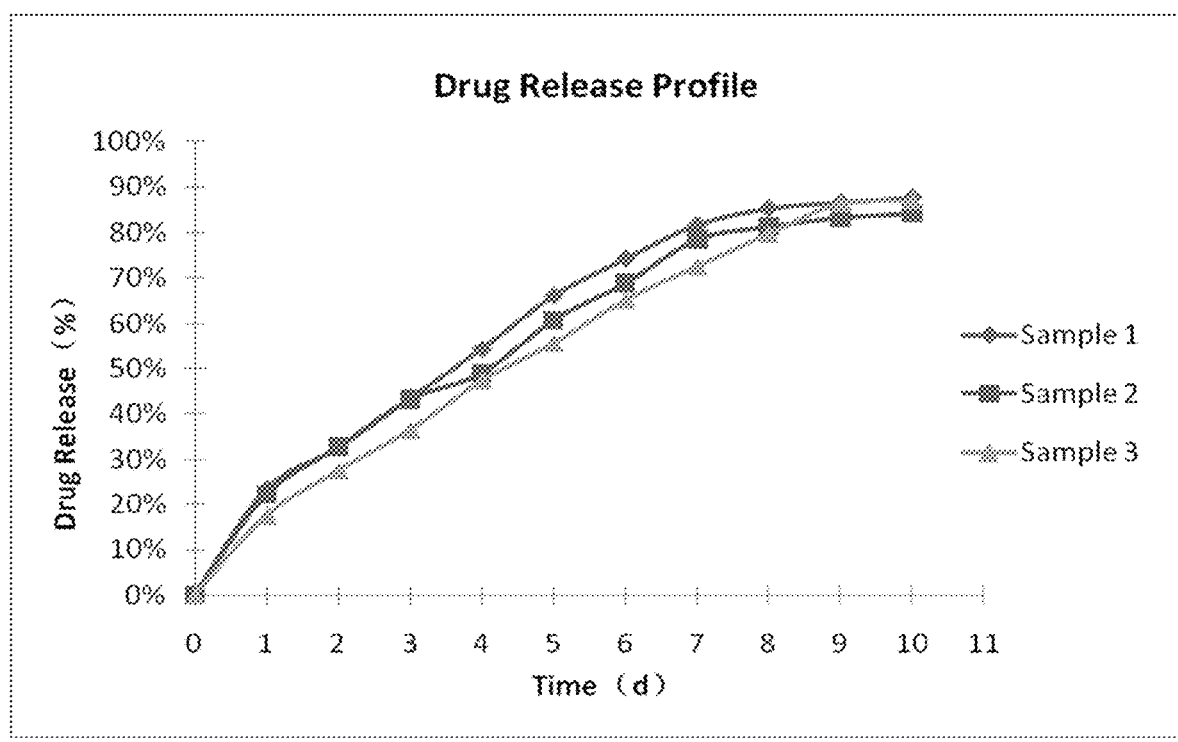
FIG. 2 depicts a graph showing the drug release profiles from cariprazine microparticles.
Figure 3:
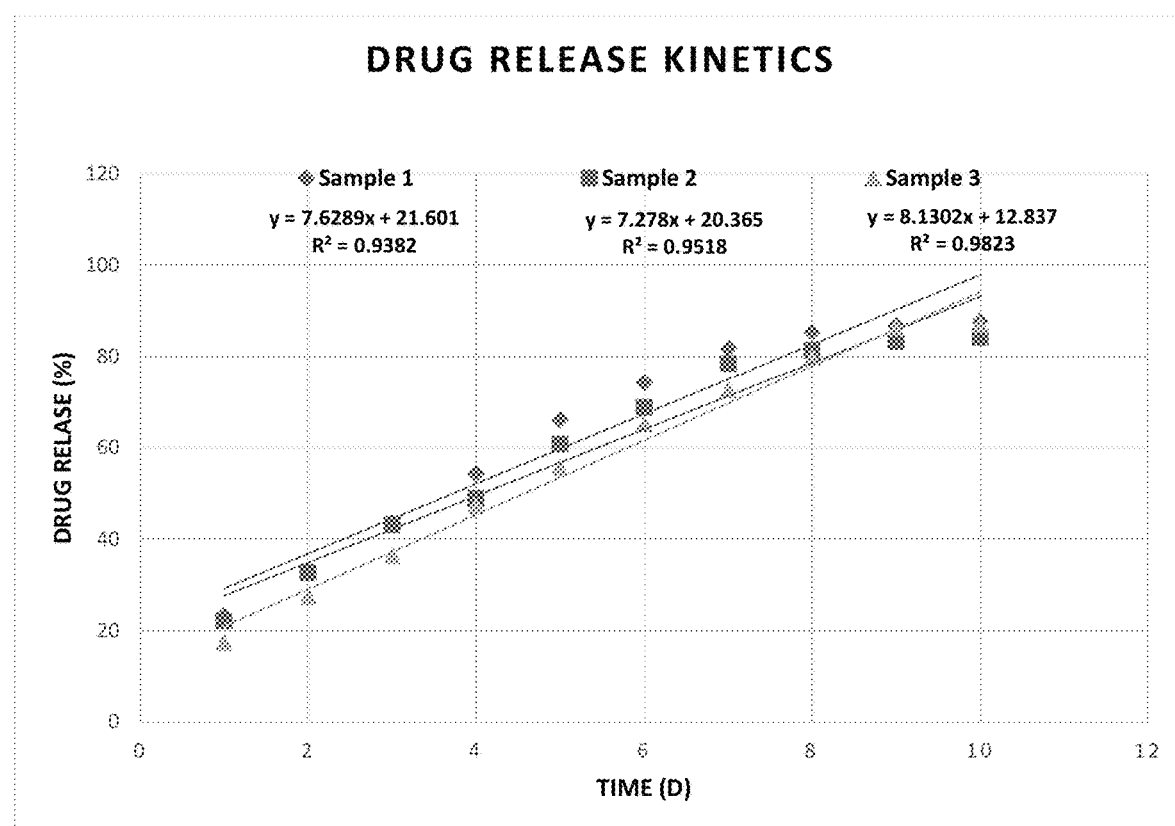
FIG. 3 depicts a graph showing the kinetics of drug release from cariprazine microparticles.

Example 5. The Drug Release Profiles and Kinetics of Cariprazine Microparticles The absorbance values are substituted into the regression equation Y=0.0154X−0.0055 to calculate the concentration. Then the concentration is multiplied by dilution factor 50, then is multiplied by 25 mL of PBS volume to obtain amount of released drug in the dissolution medium. According to the drug loading, Sample 1 microspheres contain 5.87 mg drug; Sample 2 microspheres contain 4.56 mg; and Sample 3 microspheres contain 6.58 mg. Therefore, the final percentage of drug release is 87.7% for Sample 1; 84.2% for Sample 2; and 87.1% for Sample 3. The drug release profiles are shown in FIG. 2. It was surprisingly found that the drug release follows the zero-order release kinetics, which is very favorable for the depot injection in patients, due to the fact the drug release rate is consistent during the long period of drug release, and therefore the drug blood concentration is stable over a long period after microparticle depot injection. The cariprazine is a basic drug, in which cation group complexes with the anion group of PLGA acid terminal. The complexation thus prevents the unwanted initial burst release and provides a desirable zero-order drug release kinetics from cariprazine microparticles. The zero-order release kinetics of the cariprazine microparticles in this invention are shown in FIG. 3.

The zero-order release equation for Sample 1 is $Qt=7.6289t+21.601$ ($R^2=0.9382$); for Sample 2 is $Qt=7.278t+20.365$ ($R^2=0.9518$); for Sample 3 is $Qt=8.1302t+12.837$ ($R^2=0.9823$). Qt is the percentage of the total amount released, and t is the time.

Example 6. Preparation of Cariprazine Microparticles by Solvent Extraction Method 70 mg of PLGA (50:50) polymers and 30 mg of cariprazine are dissolved in 2 mL DCM. The obtained solution is added in 20 mL of 1% PVA solution. The mixture is homogenized to obtain an emulsion. The emulsion is added to a 10% ethanol solution and stirred by a magnetic stirrer to extract DCM solvent for three hours. The hardened microspheres are sieved by a 20 µm sieve and dried in a vacuum oven to remove residual solvent and water moisture.

Example 7. Preparation of Cariprazine Microparticles by Solvent Extraction Method 70 mg of PLGA (50:50) polymers and 30 mg of cariprazine are dissolved in 2 mL ethyl acetate. The obtained solution is added in 20 mL of 1% PVA solution. The mixture is homogenized to obtain an emulsion. The emulsion is added to a 10% ethanol solution and stirred by a magnetic stirrer to extract ethyl acetate solvent for three hours. The hardened microspheres are sieved by a 20 μm sieve and dried in a vacuum oven to remove residual solvent and water moisture.

Example 8. Preparation of Cariprazine Microparticles with Two Particle Size Distribution by Solvent Extraction Method 70 mg of PLGA (50:50) polymers and 30 mg of cariprazine are dissolved in 2 mL DCM. The obtained solution is added in 20 mL of 1% PVA solution. The mixture is homogenized at low speed to obtain an emulsion with larger particle size. The emulsion is added to a 10% ethanol solution and stirred by a magnetic stirrer to extract DCM solvent for three hours. The hardened microspheres are sieved by a 50 μm sieve and dried in a vacuum oven to remove residual solvent and water moisture. Then 70 mg of PLGA (50:50) polymers and 30 mg of cariprazine are dissolved in 2 mL DCM. The obtained solution is added in 20 mL of 1% PVA solution. The mixture is homogenized at high speed to obtain an emulsion with smaller particle size. The emulsion is added to a 10% ethanol solution and stirred by a magnetic stirrer to extract DCM solvent for three hours. The hardened microspheres are sieved by a 10 μm sieve and dried in a vacuum oven to remove residual solvent and water moisture. Then two size distribution of particles are mixed aseptically to obtain a mixture of microparticles to provide a desirable drug release profile.

Example 9. Preparation of Cariprazine Microparticles with Three Particle Size Distribution by Solvent Extraction Method 70 mg of PLGA (50:50) polymers and 30 mg of cariprazine are dissolved in 2 mL DCM. The obtained solution is added in 20 mL of 1% PVA solution. The mixture is homogenized at low speed to obtain an emulsion with larger particle size. 70 mg of PLGA (50:50) polymers and 30 mg of cariprazine are dissolved in 2 mL DCM. The obtained solution is added in 20 mL of 1% PVA solution. The mixture is homogenized at medium speed to obtain an emulsion with medium particle size. Then 70 mg of PLGA (50:50) polymers and 30 mg of cariprazine are dissolved in 2 mL DCM. The obtained solution is added in 20 mL of 1% PVA solution. The mixture is homogenized at high speed to obtain an emulsion with smaller particle size. All three emulsion are mixed together and the mixed emulsion is added to a 10% ethanol solution and stirred by a magnetic stirrer to extract DCM solvent for three hours. The hardened microspheres are sieved by a 60 μm sieve and dried in a vacuum oven to remove residual solvent and water moisture.

Example 10. Preparation of Cariprazine Nanoparticles by Solvent Evaporation Method 10 mg of PLGA (50:50) polymers and 5 mg of cariprazine are dissolved in 1 mL DCM. The obtained solution is added in 20 mL of 1.0% PVA solution under magnetic stirring. The crude emulsion is sonicated by a probe sonicator for two minutes. The magnetic stirrer is used to stir the emulsion and evaporate the DCM solvent in 12 hours. The nanoparticles are obtained after filtration or centrifugation and stored for further use.

Example 11. Freeze Drying of Microspheres and Nanoparticles by Lyophilization The obtained microsphere and nanoparticles are filtered and transferred into lyophilization vials. The wet microspheres and nanoparticles in vials are quickly frozen in minus 80 degree C. freezer or in a liquid nitrogen environment. The frozen cake in vials is quickly transferred to the lyophilizer. The temperature ramping program is set from minus 40 degree C. to 15 degree C. to perform primary drying and secondary drying for three days to remove the water content in microspheres and nanoparticles. The final moisture content can be determined by a Karl Fischer titrator. The vials are sealed with dried microspheres and nanoparticles are kept in refrigerator for further use.

One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety and/or for the specific reason for which they are cited herein.

The invention claimed is:

1. A pharmaceutical composition comprising a therapeutically effective amount of an active agent selected from cariprazine, a salt thereof, or a derivative thereof, a biodegradable and biocompatible polymer comprising a polymeric matrix material, and a non-ionic water soluble colloid,
wherein the active agent is ionically complexed with the biodegradable and biocompatible polymer or the active agent is dispersed in the matrix material,
wherein the composition comprises a collection of microparticles, nanoparticles, or a combination thereof, and
wherein the cariprazine, salt thereof, or derivative thereof is present in the composition at a concentration of between about 0.1% to about 90% wt/wt.

2. The pharmaceutical composition of claim 1, wherein the biodegradable and biocompatible polymer is selected from the group consisting of poly(lactic) acid, poly(glycolic) acid, copolymers of the foregoing, poly(lactide-co-glycolide), poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, albumin, casein, lipids, and waxes.

3. The pharmaceutical composition of claim 1, wherein the collection comprises a population of microparticles or nanoparticles defined an average diameter size.

4. The pharmaceutical composition of claim 3, wherein the collection comprises two or more discreet populations of microparticles or nanoparticles, each discreet population of microparticles or nanoparticles defined an average diameter size that is different than another of the two or more discreet populations of microparticles or nanoparticles.

5. The pharmaceutical composition of claim 1, wherein the non-ionic water soluble colloid is selected from the group consisting of one or more of poly(vinyl alcohol), polysorbate, lecithin, carboxymethyl cellulose, gelatin, poly (vinyl pyrrolidone), Polysorbate 80, Polysorbate 20, or Span.

6. The pharmaceutical composition of claim 2, wherein the non-ionic water soluble colloid is selected from the group consisting of one or more of poly(vinyl alcohol), polysorbate, lecithin, carboxymethyl cellulose, gelatin, poly (vinyl pyrrolidone), polyethylene sorbitan monooleate, polyoxyethylene sorbitol ester, or sorbitan monolaurate.

7. The pharmaceutical composition of claim 1,
wherein the biodegradable and biocompatible polymer is selected from the group consisting of poly(lactic) acid, poly(glycolic) acid, copolymers of the foregoing, poly (lactide-co-glycolide), poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, albumin, casein, lipids, and waxes;

wherein the non-ionic water soluble colloid is selected from the group consisting of one or more of poly(vinyl alcohol), polysorbate, lecithin, carboxymethyl cellulose, gelatin, poly(vinyl pyrrolidone), polyethylene sorbitan monooleate, polyoxyethylene sorbitol ester, or sorbitan monolaurate, wherein the composition comprises a collection of microparticles, nanoparticles, or a combination thereof, and wherein the collection comprises one or more discreet populations of microparticles, or nanoparticles, each discreet population of microparticles, or nanoparticles defined an average diameter size that is different than another of the two or more discreet populations of microparticles, or nanoparticles.

8. The pharmaceutical composition of claim 1, wherein the biodegradable and biocompatible polymer comprises a poly (d,l-lactic co-glycolic acid) and poly(d,l-lactic acid) (d,l-PLA) copolymer, a poly(d,l-lactide-co-glycolide) copolymer, a poly (lactic acid), a poly (glycolic acid), or combination thereof.

9. The pharmaceutical composition of claim 8, wherein the copolymer is poly(d,l-lactide-co-glycolide) and the molar ratio of lactide to glycolide in the copolymer is between about 95:5 to about 5:95.

10. A pharmaceutical composition consisting essentially of a therapeutically effective amount of an active agent selected from cariprazine, a salt thereof, or a derivative thereof, a biodegradable and biocompatible polymer comprising a polymeric matrix material, and a non-ionic water soluble colloid, wherein the active agent is ionically complexed with the biodegradable and biocompatible polymer or the active agent is dispersed in the matrix material, wherein the composition is in the form of a microparticle, a nanoparticle, or a combination thereof.

* * * * *